US011471024B2

United States Patent
Wada et al.

(10) Patent No.: US 11,471,024 B2
(45) Date of Patent: Oct. 18, 2022

(54) SURGICAL IMAGING SYSTEM, IMAGE PROCESSING APPARATUS FOR SURGERY, AND METHOD FOR CONTROLLING AN IMAGING PROCEDURE

(71) Applicant: Sony Corporation, Tokyo (JP)

(72) Inventors: Seiji Wada, Kanagawa (JP); Tatsumi Sakaguchi, Kanagawa (JP); Takeshi Maeda, Tokyo (JP); Kana Matsuura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 463 days.

(21) Appl. No.: 16/493,760

(22) PCT Filed: Jan. 25, 2018

(86) PCT No.: PCT/JP2018/002245
§ 371 (c)(1),
(2) Date: Sep. 13, 2019

(87) PCT Pub. No.: WO2018/179749
PCT Pub. Date: Oct. 4, 2018

(65) Prior Publication Data
US 2020/0085282 A1 Mar. 19, 2020

(30) Foreign Application Priority Data
Mar. 27, 2017 (JP) .............................. JP2017-061261

(51) Int. Cl.
*A61B 1/00* (2006.01)
*G06F 3/01* (2006.01)

(52) U.S. Cl.
CPC ...... *A61B 1/00059* (2013.01); *A61B 1/00006* (2013.01); *A61B 1/00149* (2013.01); *G06F 3/013* (2013.01); *G06F 3/017* (2013.01)

(58) Field of Classification Search
None
See application file for complete search history.

(56) References Cited

U.S. PATENT DOCUMENTS

| 2008/0147089 | A1 | 6/2008 | Loh et al. | |
|---|---|---|---|---|
| 2014/0118518 | A1* | 5/2014 | Fructus | .................. G16Z 99/00 348/65 |
| 2014/0139018 | A1* | 5/2014 | Saunders | ................ G06F 1/266 307/18 |

(Continued)

FOREIGN PATENT DOCUMENTS

| CN | 204274388 U | 4/2015 |
|---|---|---|
| CN | 105050527 A | 11/2015 |

(Continued)

OTHER PUBLICATIONS

International Search Report and Written Opinion dated May 4, 2018 for PCT/JP2018/002245 filed on Jan. 25, 2018, 12 pages.

*Primary Examiner* — Talha M Nawaz
(74) *Attorney, Agent, or Firm* — Xsensus LLP

(57) ABSTRACT

A surgical imaging system including a surgical imaging device including identification information; a holding arm that holds and controls a position of the imaging device; a user interface configured to provide non-contact operation of the holding arm; and processing circuitry configured to control the holding arm according to the identification information and an output of the user interface.

19 Claims, 14 Drawing Sheets

(56) References Cited

U.S. PATENT DOCUMENTS

2016/0015471 A1* 1/2016 Piron .................... A61B 1/045
                                                        600/424
2017/0296292 A1* 10/2017 Mahmood .............. A61B 34/37
2017/0304007 A1* 10/2017 Piron .................... A61B 1/045

FOREIGN PATENT DOCUMENTS

| CN | 106413510 A | 2/2017 |
|----|----|----|
| JP | S62-166312 A | 7/1987 |
| JP | 09-028713 A | 2/1997 |
| JP | 2003070803 A | 3/2003 |
| JP | 2006221117 A | 8/2006 |
| WO | 2013/027203 A1 | 2/2013 |
| WO | 2014/139018 A1 | 9/2014 |
| WO | 2015/042460 A1 | 3/2015 |
| WO | WO-2018159338 A1 | 9/2018 |

* cited by examiner

ON SCREEN
PIVOT ∠φp(SCREEN HORIZONTAL ANGLE,deg) ∠θp(SCREEN VERTICAL ANGLE,deg)

↓ CONVERSION: TROCAR POINT SYMMETRY

CAMERA ARM COMMAND
PANTILTROLL - Δφc(SCREEN HORIZONTAL ANGLE) - Δθc(SCREEN VERTICAL ANGLE)
Move Δzc(AXIAL DIRECTION DEPTH)
CAMERA COMMAND
Crop ΔX(SCREEN %) ΔY(SCREEN %) Δa(MAGNIFICATION)

Fig. 14

|  |  | OPTICAL ZOOM | MOVE |
|---|---|---|---|
| VM | SCREEN UI COMMAND | ZOOM $\Delta$a (MAGNIFICATION) | MOVE $\Delta$X (SCREEN %) $\Delta$Y (SCREEN %) |
| VM | CAMERA ARM COMMAND |  | MOVE $\Delta$X (ABSOLUTE DISTANCE) $\Delta$Y (ABSOLUTE DISTANCE) |
| VM | CAMERA COMMAND | ZOOM $\Delta$a (MAGNIFICATION) |  |
| FRONT VIEW SCOPE | SCREEN UI COMMAND | ZOOM $\Delta$a (MAGNIFICATION) | MOVE $\Delta$X (SCREEN %) $\Delta$Y (SCREEN %) |
| FRONT VIEW SCOPE | CAMERA ARM COMMAND | MOVE $\Delta$z (AXIAL DIRECTION DEPTH) | PTR- $\Delta\phi$c (HORIZONTAL ANGLE) - $\Delta\theta$c (VERTICAL ANGLE) |
| FRONT VIEW SCOPE | CAMERA COMMAND | FOCUS d+ $\Delta$R (AXIAL DIRECTION FOCAL LENGTH) | MOVE $\Delta$z (AXIAL DIRECTION DEPTH) |

|  |  | PIVOT | PAN/TILT/ROLL |
|---|---|---|---|
| VM | SCREEN UI COMMAND | PIVOT $\Delta\phi$c (HORIZONTAL ANGLE) $\Delta\theta$p (VERTICAL ANGLE) | PTR $\Delta\phi$c (HORIZONTAL ANGLE) $\Delta\theta$c (VERTICAL ANGLE) $\Delta\theta$r (ROTATION ANGLE) |
| VM | CAMERA ARM COMMAND | PIVOT $\Delta\phi$c (HORIZONTAL ANGLE) $\Delta\theta$c (VERTICAL ANGLE) RADIUS d | PTR $\Delta\phi$c (HORIZONTAL ANGLE) $\Delta\theta$c (VERTICAL ANGLE) $\Delta\theta$r (ROTATION ANGLE) |
| VM | CAMERA COMMAND |  |  |
| FRONT VIEW SCOPE | SCREEN UI COMMAND | PTR- $\Delta\phi$c (HORIZONTAL ANGLE) - $\Delta\theta$c (VERTICAL ANGLE) | PTR- $\Delta\phi$c (HORIZONTAL ANGLE) $\Delta\theta$c (VERTICAL ANGLE) $\Delta\theta$r (ROTATION ANGLE) |
| FRONT VIEW SCOPE | CAMERA ARM COMMAND | PTR- $\Delta\phi$c (HORIZONTAL ANGLE) - $\Delta\theta$c (VERTICAL ANGLE) | PTR- $\Delta\phi$c (HORIZONTAL ANGLE) $\Delta\theta$c (VERTICAL ANGLE) $\Delta\theta$r (ROTATION ANGLE) |
| FRONT VIEW SCOPE | CAMERA ARM COMMAND | MOVE $\Delta$zc (AXIAL DIRECTION DEPTH) |  |
| FRONT VIEW SCOPE | CAMERA COMMAND | CROP $\Delta$X (SCREEN %) $\Delta$Y (SCREEN %) $\Delta$s (MAGNIFICATION) |  |

SURGICAL IMAGING SYSTEM, IMAGE PROCESSING APPARATUS FOR SURGERY, AND METHOD FOR CONTROLLING AN IMAGING PROCEDURE

CROSS REFERENCE TO RELATED APPLICATIONS

This application is based on PCT filing PCT/JP2018/002245, filed Jan. 25, 2018, which claims the benefit of Japanese Priority Patent Application JP 2017-061261, filed Mar. 27, 2017, the entire contents of each are incorporated herein by reference.

TECHNICAL FIELD

The present disclosure relates to a control device of a medical system, a control method of a medical system, and a medical system.

BACKGROUND ART

For example, below Patent Literature 1 describes a past technology that inserts a trocar in an abdominal wall, and inserts a scope, which is a laparoscope, in a hole of the trocar, and displays on a TV monitor an observed image in an abdominal cavity detected by the scope.

CITATION LIST

Patent Literature
  PTL 1: JP H9-28713A

SUMMARY

Technical Problem

For example, a surgical imaging device such as a video endoscope like a laparoscope described in above Patent Literature 1 is sometimes used to display an observed image on the monitor, and a video microscope is sometimes used in surgical operation or the like. If how to operate differs depending on the difference of device and use environment, there is a problem that the operability to move and expand an area of the observed image displayed on the monitor deteriorates for a user who performs surgical operation or the like while watching the monitor.

Hence, the behavior of an imaging device is to be controlled by the same or similar operation, even when there is a difference related to the imaging device for capturing an image of a human body.

Solution to Problem

According to an embodiment of the present disclosure, there is provided a surgical imaging system including a surgical imaging device including identification information; a holding arm that holds and controls a position of the surgical imaging device; a user interface configured to provide non-contact operation of the holding arm; and processing circuitry configured to control the holding arm according to the identification information and an output of the user interface.

Further, according to an embodiment of the present disclosure, there is provided an image processing apparatus for surgery including processing circuitry configured to control a holding arm that holds and controls a position of an imaging device according to identification information of the imaging device and an output of a user interface configured to provide non-contact operation of the holding arm.

Further, according to an embodiment of the present disclosure, there is provided a method for controlling an imaging procedure including identifying, using processing circuitry, a surgical imaging device including identification information; determining a non-contact input of a user; and controlling a holding arm holds and controls a position of the surgical imaging device according to the identification information and the determined non-contact input of the user.

Advantageous Effects of Invention

As described above, according to an embodiment of the present disclosure, the behavior of the imaging device is controlled by the same or similar operation, even when there is a difference related to the imaging device for capturing an image of a human body.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 14 is a schematic diagram coordinating a relationship between commands on a screen illustrated in FIGS. 7 to 13, a camera arm command, and a camera command, with regard to each of zoom, move, pivot, and pan/tilt/roll.

DESCRIPTION OF EMBODIMENTS

Figure 1:
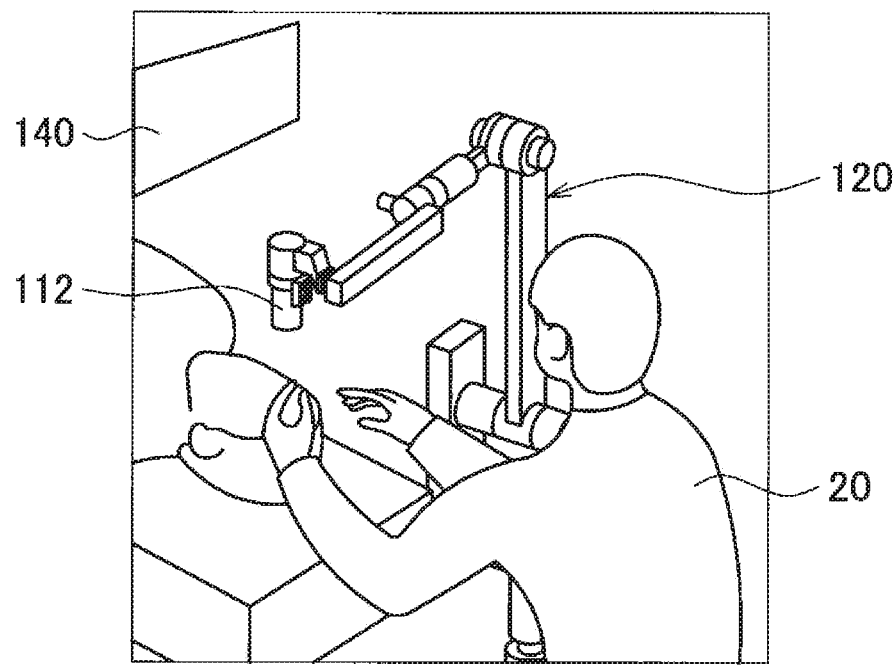
FIG. 1 is a schematic diagram illustrating a medical device according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Figure 2:
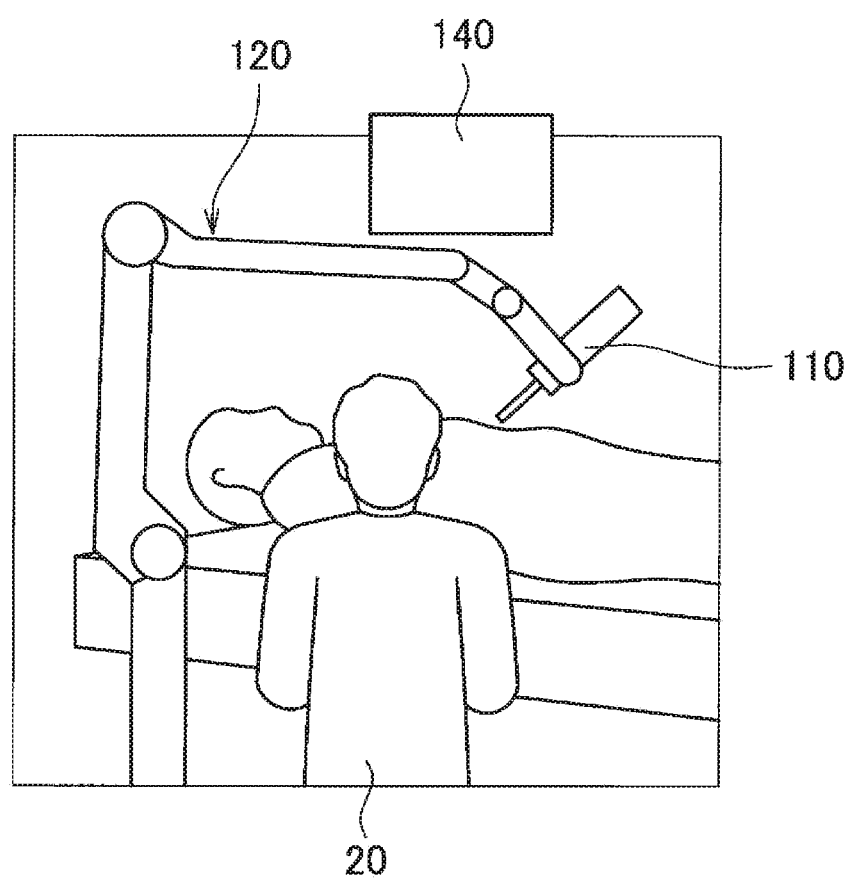
FIG. 2 is a schematic diagram illustrating a medical device according to an embodiment of the present disclosure.

Note that description will be made in the following order.
1. A medical device as a target of the present embodiment
2. A configuration example of a system relevant to a video endoscope
3. A configuration example of a system relevant to a video microscope
4. A block configuration example of a system that includes a control device
5. With regard to conversion from a command by a surgeon to control information
6. Generation of control information that refers to identification information 1. A Medical Device as a Target of the Present Embodiment FIGS. 1 and 2 are schematic diagrams illustrating a medical device according to an embodiment of the present disclosure. FIG. 1 illustrates a video microscope 112, and FIG. 2 illustrates a video endoscope (a laparoscope 110), as a medical device. Both of the video microscope 112 and the laparoscope 110 are supported by a camera arm 120 (a support arm device), and is moved to a desired position by driving of the camera arm 120. A camera image of the video microscope 112 or the laparoscope 110 is displayed on a display 140. The video microscope 112 or the laparoscope 110 is controlled by hand operation or hands-free operation by a surgeon 20 who is a user. Although the laparoscope 110 is illustrated as a video endoscope, the video endoscope may be other than the laparoscope 110.

2. A Configuration Example of a System Relevant to a Video Endoscope

Figure 3:
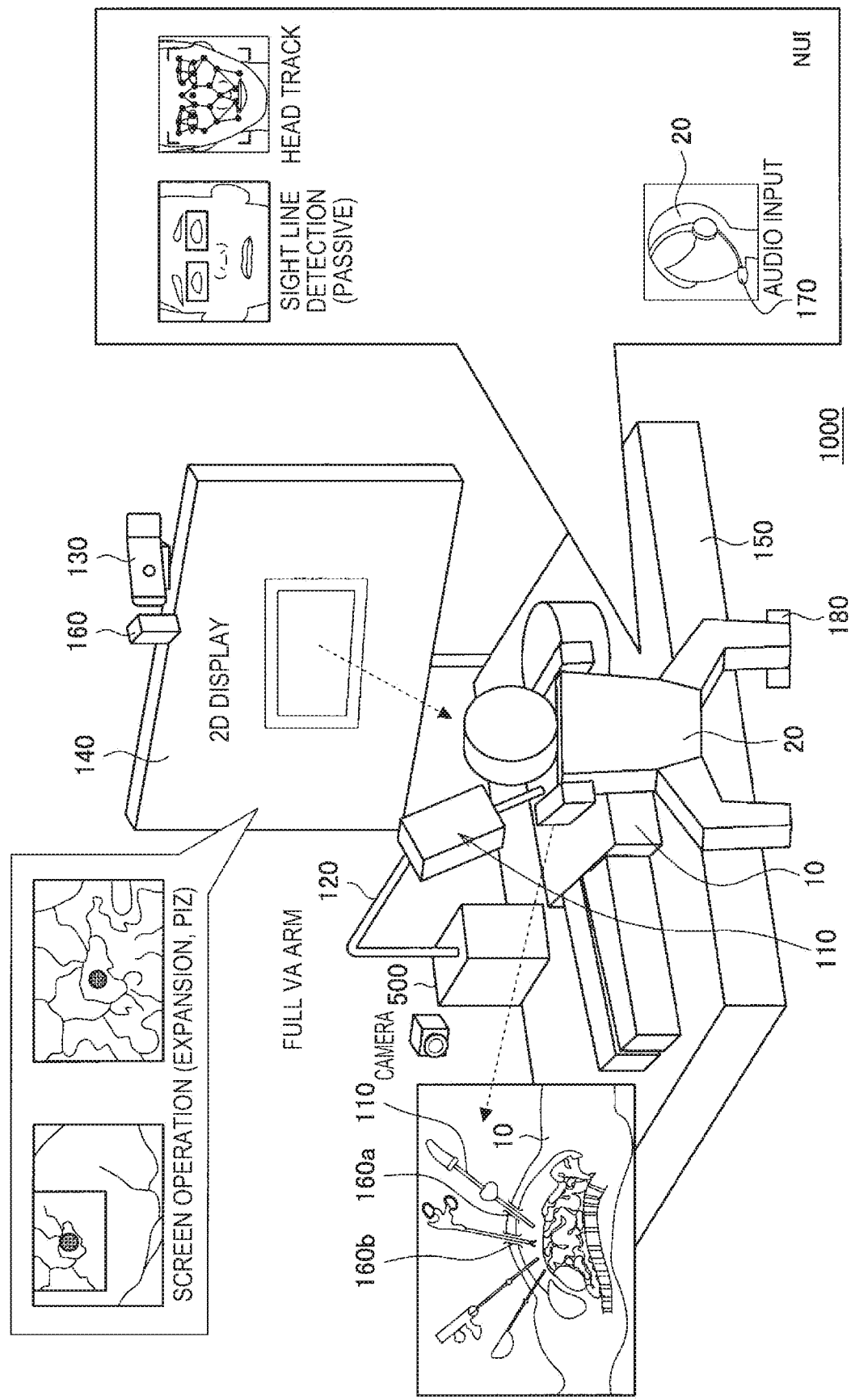
FIG. 3 is a schematic diagram illustrating a schematic configuration of a surgical operation system according to an embodiment of the present disclosure.

A schematic configuration of a surgical operation system 1000 according to an embodiment of the present disclosure will be described with reference to FIG. 3. The surgical operation system 1000 illustrated in FIG. 3 illustrates a system of the video endoscope, and particularly relates to a system that performs surgical operation by the laparoscope 110. In the laparoscope surgical operation, a plurality of holes are opened in an abdominal part of a patient 10, and the laparoscope 110 and operation tools, such as forceps, a suction device, and an electric scalpel, are inserted from the holes, and the surgical operation is performed with the operation tools, while the inside of an abdominal cavity is visually confirmed by the laparoscope 110. The laparoscope 110 is rotatable about a center at a trocar 160a. FIG. 3 is a schematic diagram illustrating a positional relationship between the patient 10, the surgeon 20, and the laparoscope 110, in the laparoscope surgical operation system that uses the laparoscope 110. Note that the surgeon 20 is an operating surgeon or a scopist, for example.

The surgical operation system 1000 includes the laparoscope 110, the camera arm 120, a behavior recognition camera 130, the display 140, an operating table 150, a sight line detection camera 160, a microphone 170, a foot switch 180, and a control device 500. The laparoscope 110 is a device, such as a 3D camera held by the camera arm 120.

The laparoscope 110 is inserted into the body of the patient 10 and captures an image of the situation inside the body. The laparoscope 110 transmits an image obtained as a result of the imaging, as an operative field image, to the control device 500.

The camera arm 120 holds the laparoscope 110, and controls the position and the angle of the laparoscope 110. The behavior recognition camera 130 is a 2D camera for example, and is located on the display 140. The behavior recognition camera 130 captures an image of the surgeon 20, and recognizes the behavior of the surgeon 20. A marker may be attached to the surgeon 20, in order to make it easy for the behavior recognition camera 130 to recognize the behavior of the surgeon 20. The behavior recognition camera 130 transmits a 2D image obtained as a result of the imaging, as a surgeon image, to the control device 500.

The display 140 includes a comparatively large screen, and is located at a position comparatively remote from the surgeon 20. In the example of FIG. 3, the display 140 is located at a position that faces the surgeon 20 with the operating table 150 in between. The operative field image transmitted from the control device 500 is displayed on the display 140. The display 140 is configured with a 3D display. The surgeon 20 recognizes the operative field image displayed on the display 140, as a 3D image, with naked eyes.

The control device 500 sets an operation mode to a hand operation mode or a hands-free mode. The hand operation mode is a mode in which the surgical operation system 1000 is controlled on the basis of an input by hands of the surgeon 20 (for example, force application to the camera arm 120, and operation of an operation button and the like (not illustrated in the drawings) provided in each unit). The hands-free mode is a mode in which the surgical operation system 1000 is controlled, not by the hands of the surgeon 20, but on the basis of a non-contact input such as voice, sight line, motion and direction of a head, gesture, and an input by the contact of a leg portion to the foot switch 180.

Also, the control device 500 receives a surgeon image transmitted from the behavior recognition camera 130, and detects the position of the head of the surgeon 20 in the surgeon image, and detects the motion of the head (head tracking) and the direction of the head. Further, the control device 500 recognizes the gesture of the surgeon 20 from the surgeon image.

Also, the control device 500 receives information indicating the direction of the sight line of the surgeon 20 transmitted from the sight line detection camera 160, and recognizes the position of the sight line on the screen of the display 140, on the basis of the information and the position and the direction of the head of the surgeon 20. Also, the control device 500 receives a voice transmitted from the microphone 170, and performs voice recognition to the voice. Also, the control device 500 receives an operation signal that indicates the operation to the foot switch 180 transmitted from the foot switch 180, and recognizes the detail of the operation to the foot switch 180 on the basis of the operation signal.

Further, when the operation mode is the hands-free mode, the control device 500 uses, as the input information, the motion and the direction of the head of the surgeon 20, the gesture of the surgeon 20, sight line position information that indicates the position of the sight line on the screen of the display 140, a voice recognition result, a sound volume, and operation information that indicates the detail of the operation to the foot switch 180. The control device 500 recognizes a command from the surgeon 20 and the state of the surgeon 20 on the basis of the input information.

The control device 500 authorizes the command from the surgeon 20, depending on the state of the surgeon 20. The control device 500 controls the imaging of the laparoscope 110, and controls the driving of the camera arm 120, and controls the displaying of the display 140, and changes the operation mode, in accordance with the authorized command.

The microphone 170 is attached to the surgeon 20. The microphone 170 acquires voices of the environment that includes the voice of the surgeon 20, and transmits the voices to the control device 500. The foot switch 180 is located around the surgeon 20, and is operated by the contact of the foot of the surgeon 20. The foot switch 180 transmits, to the control device 500, an operation signal that indicates the foot operation from the surgeon 20.

In the surgical operation system 1000 configured as described above, the surgeon 20 lays the patient 10 on the operating table 150, and performs the action of the surgical operation, while watching the operative field image displayed on the display 140.

Also, the surgeon 20 performs a non-contact input or an input by the contact operation of the foot or the like, when changing the operation mode, the imaging condition of the laparoscope 110, the position and the angle of the laparoscope 110, the displaying of the display 140, etc. Thus, the surgeon 20 can perform the input while gripping the operation tools.

Note that the sight line detection method, the detection method of the gesture and the motion and the direction of the head of the surgeon 20, the voice acquisition method, and the like can employ an arbitrary method.

As described above, in the system 1000 illustrated in FIG. 3, the laparoscope 110 is held by the camera arm 120, and the surgeon 20 controls the attitude of the laparoscope 110, while watching the image captured by the laparoscope 110 on the display 140.

3. A Configuration Example of a System Relevant to a Video Microscope

Figure 4:
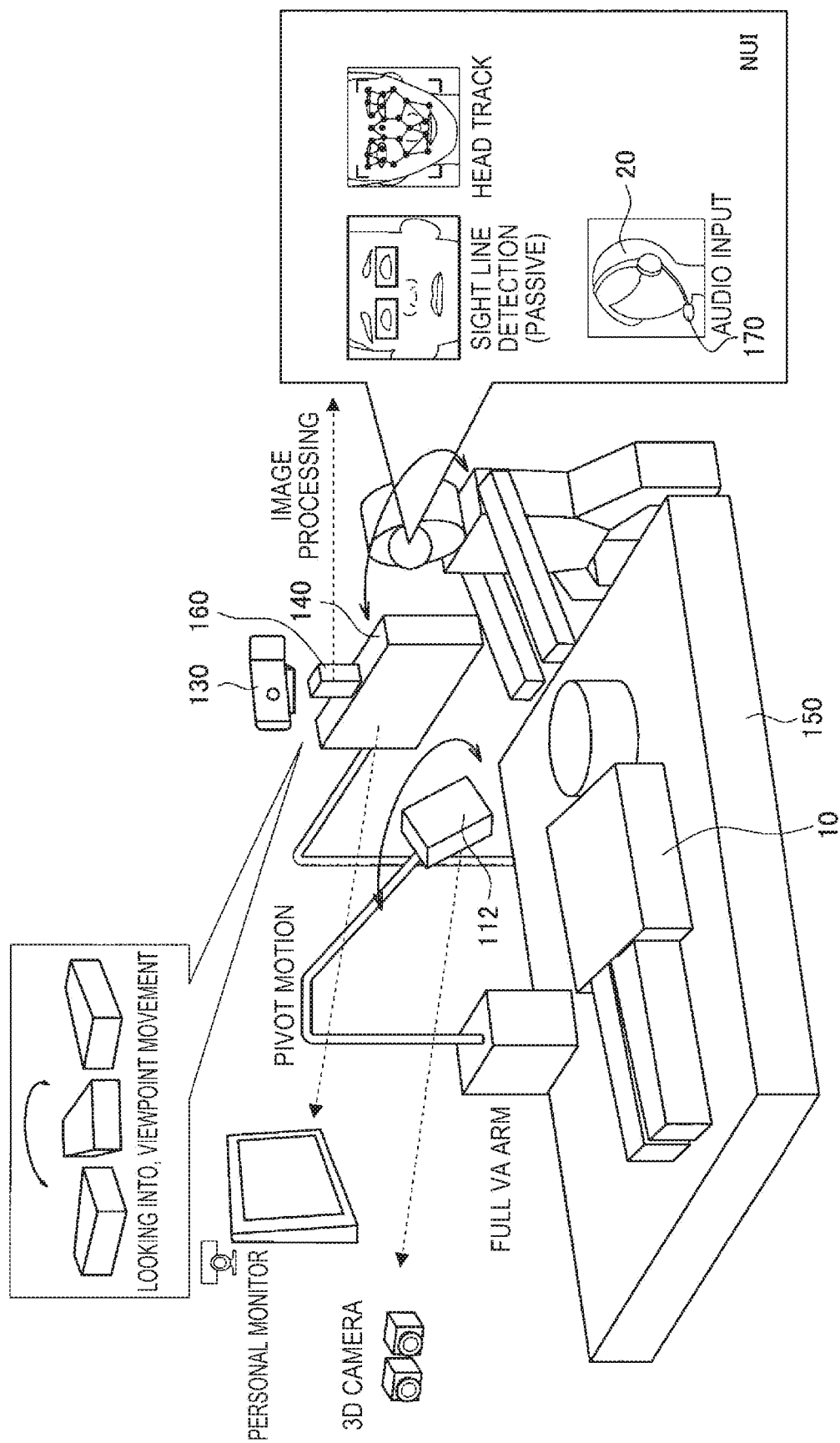
FIG. 4 is a schematic diagram illustrating a configuration of a system relevant to a video microscope.
Figure 5:
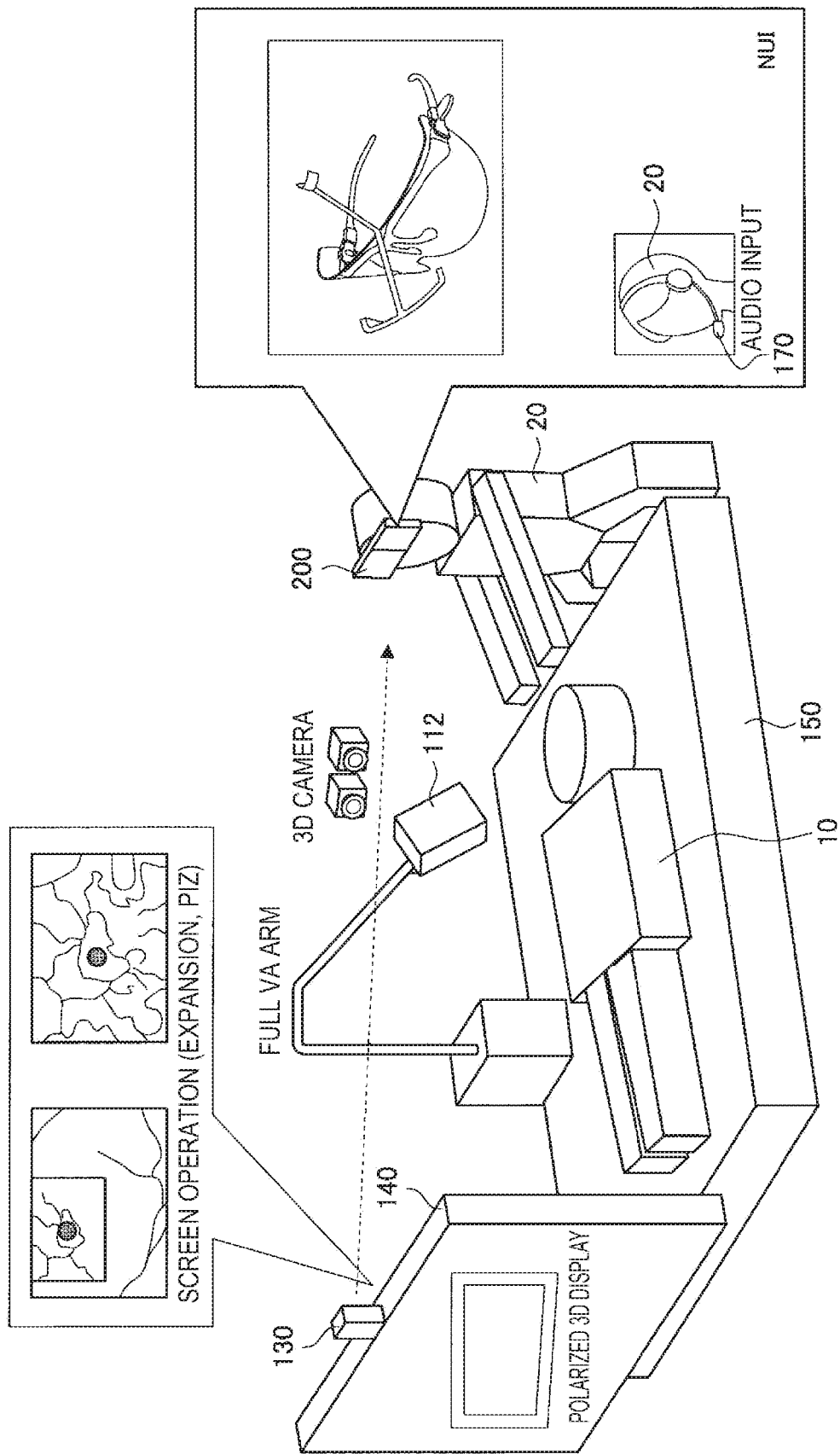
FIG. 5 is a schematic diagram illustrating a configuration of a system relevant to a video microscope.

FIGS. 4 and 5 are schematic diagrams illustrating a configuration of the system 1000 relevant to the video microscope. In the system illustrated in FIGS. 4 and 5, the video microscope 112 is attached to the camera arm 120, instead of the laparoscope 110 of FIG. 3.

The image captured by the video microscope 112 is displayed on the display 140, in the system 1000 illustrated in FIG. 4. The surgeon 20 can operate the video microscope 112, while visually confirming the image of the display 140, similarly to FIG. 3.

Although the system 1000 illustrated in FIG. 5 is a system relevant to the video microscope 112 similarly to FIG. 4, the surgeon 20 wears eyeglasses 200 on the head, unlike FIG. 4. The eyeglasses 200 are configured with 3D polarized eyeglasses and a sight line detection device. The surgeon 20 can recognize the operative field image displayed on the display 140 as a 3D image, by watching the display 140 via the 3D polarized eyeglasses of the eyeglasses 200. Also, the surgeon 20 inputs the sight line into the eyeglasses 200, by watching the environment via the eyeglasses 200. The sight line detection device of the eyeglasses 200 detects the sight line of the surgeon 20, and transmits the information indicating the direction of the sight line to the control device 500.

4. A block Configuration Example of a System that Includes a Control Device

Figure 6:
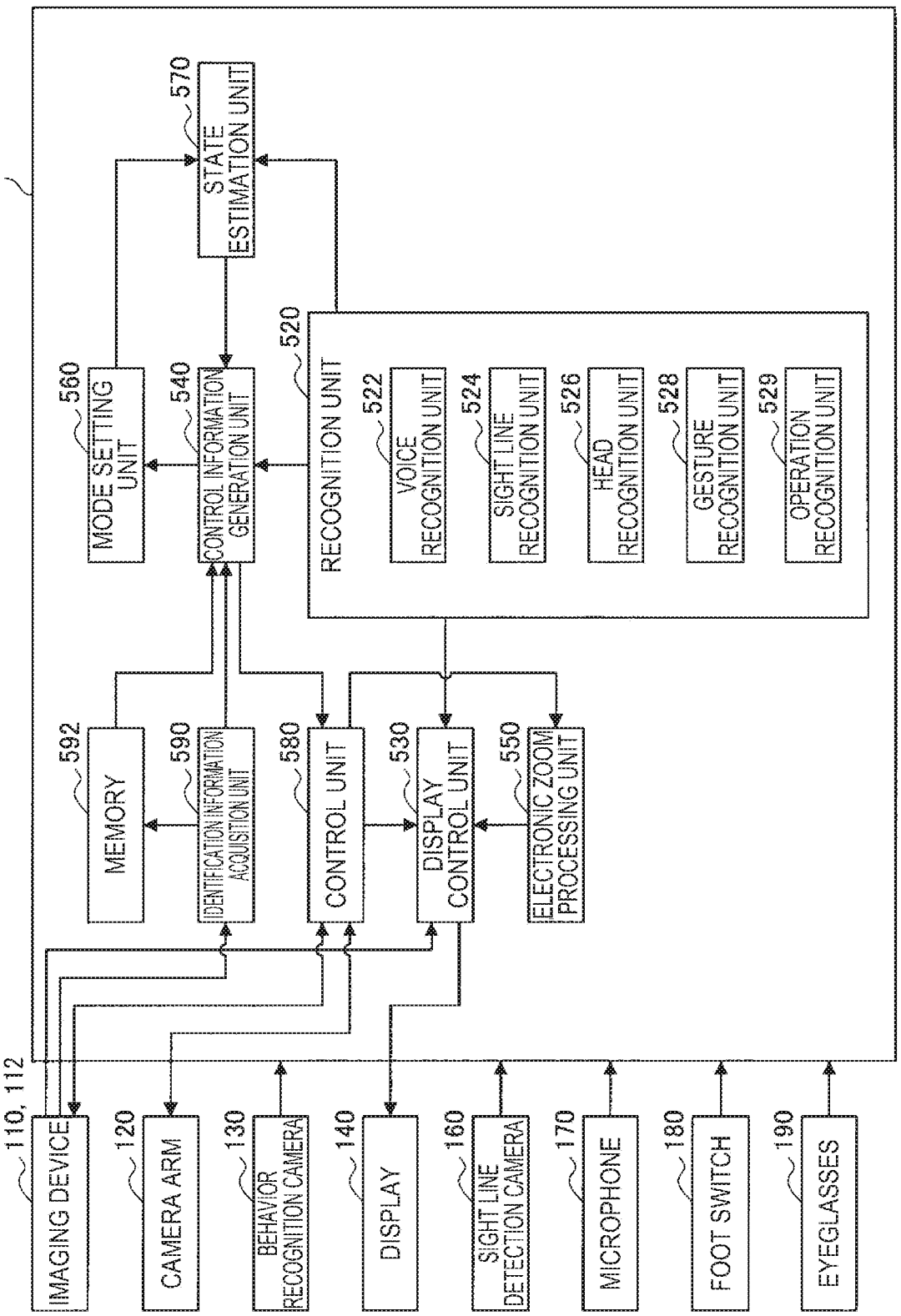
FIG. 6 is a block diagram illustrating a configuration of a system that includes a control device.

FIG. 6 relates to the systems illustrated in FIGS. 3 to 5, and is a block diagram illustrating the configuration of the system 1000 that includes the control device 500. As illustrated in FIG. 6, the camera (the imaging device; the laparoscope 110 or the video microscope 112), the camera arm 120, the behavior recognition camera 130, the display 140, the sight line detection camera 160, the microphone 170, the foot switch 180, and the eyeglasses 190 are connected to the control device 500. In FIG. 6, the configuration of the laparoscope 110 includes a camera control unit (CCU) that controls the focal point position and the focal length of the laparoscope 110. Note that, in FIG. 6, the sight line detection camera 160 is provided in the eyeglasses 200, in the case of the system illustrated in FIG. 5.

The following description assumes that the camera is the laparoscope 110. The control device 500 adjusts the spatial position and the angle of the laparoscope 110, in accordance with the instruction of the surgeon 20. In the present embodiment, when the surgeon 20 issues an instruction, the instruction is issued without hands on the basis of the direction of the sight line, the motion of the head, the voice, and the like, in addition to the instruction by the foot switch 180. The instruction information corresponding to the instruction of the surgeon 20 is sent to the control device 500.

The control device 500 includes a recognition unit 520, a display control unit 530, a control information generation unit 540, an electronic zoom processing unit 550, a mode setting unit 560, a state estimation unit 570, a control unit 580, an identification information acquisition unit 590, and a memory 592. The recognition unit 520 is a user interface configured with a voice recognition unit 522, a sight line recognition unit 524, a head recognition unit 526, a gesture recognition unit 528, and an operation recognition unit 529. The components of the control device 500 illustrated in FIG. 6 are configured with a circuit (hardware), or a central processing unit such as a CPU and a program (software) for functioning the central processing unit.

The voice recognition unit 522 performs voice recognition to the voice transmitted from the microphone 170, and recognizes a speech as the non-contact input of the surgeon 20. Also, the voice recognition unit 522 recognizes the sound volume of the voice transmitted from the microphone 170, as the non-contact input of the surgeon 20. The voice recognition unit 522 supplies the speech and the sound volume which are the voice recognition result, as the input information, to the control information generation unit 540.

The sight line recognition unit 524 recognizes the position of the sight line on the screen of the display 140, as the non-contact input of the surgeon 20, on the basis of the information indicating the direction of the sight line transmitted from the sight line detection camera 160 and the position and the direction of the head recognized by the head recognition unit 526. The sight line recognition unit 524 supplies the sight line position information indicating the position, as the input information, to the control information generation unit 540, the state estimation unit 570, and the display control unit 530.

The head recognition unit 526 recognizes the position, the motion, and the direction of the head of the surgeon 20, as the non-contact input from the surgeon 20, by detecting the position of the surgeon 20 from the surgeon image transmitted from the behavior recognition camera 130. The head recognition unit 526 supplies the motion and the direction of the head, as the input information, to the control information generation unit 540 and the state estimation unit 570. Also, the head recognition unit 526 supplies the position and the direction of the head to the sight line recognition unit 524.

The gesture recognition unit 528 recognizes the input of the gesture of the surgeon 20, as the non-contact input of the surgeon 20, from the surgeon image transmitted from the behavior recognition camera 130. The gesture recognition unit 528 supplies the gesture of the surgeon 20, as the input information, to the control information generation unit 540.

The operation recognition unit 529 receives the operation signal transmitted from the foot switch 180, and recognizes the detail of the operation to the foot switch 180, as the input by the contact from the surgeon 20. The operation recognition unit 529 supplies the operation information that indicates the detail of the operation, as the input information, to the control information generation unit 540. Also, the operation recognition unit 529 can receive an operation signal input from an operation member, such as a keyboard and a mouse.

The control information generation unit 540 recognizes the command from the surgeon 20 on the basis of the input information supplied from the recognition unit 520, and generates control information for controlling the camera arm 120 on the basis of the command. When the recognized command is a command for changing the operation mode, the control information generation unit 540 reports the command to the mode setting unit 560 that sets the mode on the basis of the command.

The identification information acquisition unit 590 acquires the identification information of the camera, when the camera, such as the laparoscope 110 and the video endoscope 112, is connected. The acquired identification information is temporarily stored in the memory 592.

The mode setting unit 560 sets the operation mode to the hand operation mode or the hands-free mode, in accordance with the command supplied from the control information generation unit 540. The mode setting unit 560 supplies the set operation mode to the state estimation unit 570.

When the operation mode supplied from the mode setting unit 560 is the hands-free mode, the state estimation unit 570 estimates the state of the surgeon 20 on the basis of the input information supplied from the recognition unit 520. The state estimation unit 570 reports the estimated state to the control information generation unit 540.

The control unit 580 executes the command on the basis of the control information supplied from the control information generation unit 540. Specifically, when the control information supplied from the control information generation unit 540 is the control information relevant to the imaging control of the laparoscope 110, the control unit 580 performs the imaging control of the laparoscope 110 in accordance with the control information. Thereby, various types of imaging functions, such as an electronic zoom function of the laparoscope 110, is controlled.

Also, when the control information supplied from the control information generation unit 540 is the command relevant to the drive control of the camera arm 120, the control unit 580 performs the drive control of the camera arm 120 in accordance with the control information. The camera arm 120 includes a plurality of joints and actuators provided in the respective joints, as an example. The actuator of each joint is driven by the control of the control unit 580, and the behavior of the camera arm 120 corresponding to the control information is performed. Also, when the command supplied from the control information generation unit 540 is the control information relevant to the display control of the display 140, the control unit 580 controls the display control unit 530 by supplying the control information to the display control unit 530.

The display control unit 530 performs a process for displaying, on the display 140, the operative field image transmitted from the laparoscope 110. Also, when the control information supplied from the control unit 580 is an annotation display command, the display control unit 530 superimposes a mark at a position that corresponds to the sight line of the surgeon 20 in the operative field image transmitted from the laparoscope 110, on the basis of the sight line position information supplied from the sight line recognition unit 524. Then, the display control unit 530 supplies, to the display 140, the operative field image on which the mark is superimposed, and displays the operative field image.

Further, when the command supplied from the control unit 580 is a menu display command for displaying a graphical user interface (GUI) such as a menu button on the display 140, the display control unit 530 superimposes the image of the GUI in the operative field image transmitted from the laparoscope 110. The display control unit 530 supplies, to the display 140, the operative field image on which the GUI is superimposed, and displays the operative field image.

For example, when the voice recognition result in the input information is "zoom in", and the sight line position information indicates a position in the screen of the display 140, the control information generation unit 540 recognizes that the command from the surgeon 20 is a command that causes the laparoscope 110 to zoom in and capture an image around a center at the imaging subject that corresponds to the position of the sight line indicated by the sight line position information. Then, the control information generation unit 540 generates the control information for executing the recognized command.

Similarly, when the voice recognition result in the input information is "zoom out", and the sight line position information indicates a position in the screen of the display 140, the control information generation unit 540 recognizes that the command from the surgeon 20 is a command that causes the laparoscope 110 to zoom out around a center at the imaging subject that corresponds to the position of the sight line indicated by the sight line position information. Then, the control information generation unit 540 generates the control information for executing the recognized command.

Also, when the voice recognition result in the input information is "focus", and the sight line position information indicates a position in the screen of the display 140, the control information generation unit 540 recognizes that the command from the surgeon 20 is a command for performing focus control of the laparoscope 110 to focus at the imaging subject that corresponds to the position of the sight line indicated by the sight line position information. Then, the control information generation unit 540 generates the control information for executing the recognized command.

As described above, the surgeon 20 inputs the detail of the imaging control with the voice suitable for the command input, and inputs the position necessary for the imaging control with the sight line suitable for the position input. Thus, the surgeon 20 can easily issue the command relevant to the imaging control.

Also, when the voice recognition result in the input information is "pivot", and the sight line position information indicates a position in the screen of the display 140, and the sight line position information does not change temporally, and the motion of the head of the surgeon 20 is movement, and the operation information indicates pressing of the foot switch 180, the control information generation unit 540 recognizes that the command from the surgeon 20 is a command for controlling the camera arm 120 in such a manner that the laparoscope 110 makes a pivot motion in response to the motion of the head. Then, the control information generation unit 540 generates the control information for executing the recognized command.

When the voice recognition result in the input information is "slide", and the motion of the head of the surgeon 20 is rotation, and the sight line position information indicates a position in the screen of the display 140, and the direction of the temporal change of the position indicated by the sight line position information is the same as the rotation direction of the head, and the operation information indicates pressing of the foot switch 180, the control information generation unit 540 recognizes that the command from the surgeon 20 is a command for controlling the camera arm 120 in such a manner that the laparoscope 110 makes a slide motion in response to the position of the sight line. Then, the control information generation unit 540 generates the control information for executing the recognized command.

Note that the pivot motion command and the slide motion command are commands relevant to drive control of the camera arm 120, and therefore the type of the these commands is classified into camera arm control.

5. With Regard to Conversion From a Command by a Surgeon to Control Information

The command that the surgeon 20 issues while watching the display 140 is recognized by the recognition unit 520, and the control information is generated by the control information generation unit 540. In the following, a method for converting the command that the surgeon 20 issues while watching the display 140, to a camera arm command for operating the camera arm 120 and a camera command for operating the camera (the laparoscope 110, the video microscope) will be described.

The surgeon 20 uses a zoom command, a move command for causing the camera to make a translation motion, a pivot command for causing the camera to pivot in relation to the object, a pan/tilt/roll command of the camera, as the command used while watching the video screen. The two-dimensional move, the pivot, and the pan/tilt/roll command are used as the camera arm command for the video microscope 112, and the zoom is used as the camera command. Three dimensional move and the pan/tilt/roll command are used as the camera arm command in the case of the laparoscope 110. The commands to the camera arm 120 and the camera are different between the case of the video microscope 112 and the case of the laparoscope 110, but the commands used by the surgeon 20 are the same.

Figure 7:
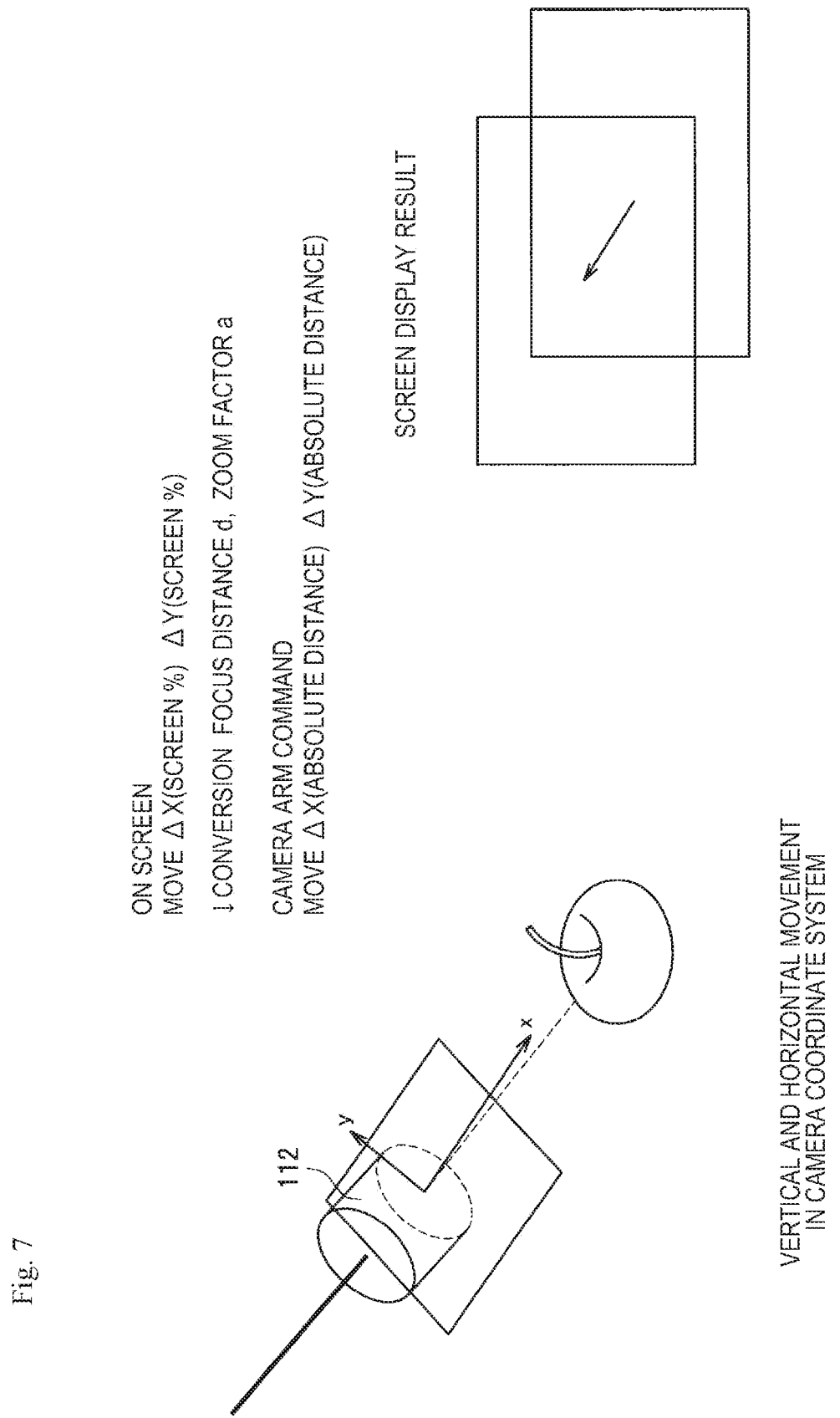
FIG. 7 is a schematic diagram illustrating a conversion method from a command on a screen of a display to a command of a camera arm, in a system of a video microscope.

FIGS. 7 to 10 are schematic diagrams illustrating a conversion method from the command on the screen of the display 140 to the command of the camera arm, in the system 1000 of the video microscope 112. FIG. 7 illustrates a case in which the move command on the screen by the surgeon 20 is converted. The move command on the screen is input as a change amount ($\Delta X$, $\Delta Y$) of XY coordinates on the screen. This change amount ($\Delta X$, $\Delta Y$) is indicated by a proportion (%) in the length in the X direction or the Y direction of the screen. The change amount ($\Delta X$, $\Delta Y$) on the screen is converted to the spatial coordinate system and is output as the camera arm command, on the basis of a distance between the camera and the imaging subject (the imaging subject distance d) corresponding to the state of the camera arm 120 and a zoom factor a corresponding to the camera state. In this case, the camera arm command is $\Delta X$, $\Delta Y$, which are absolute distances.

Figure 8:
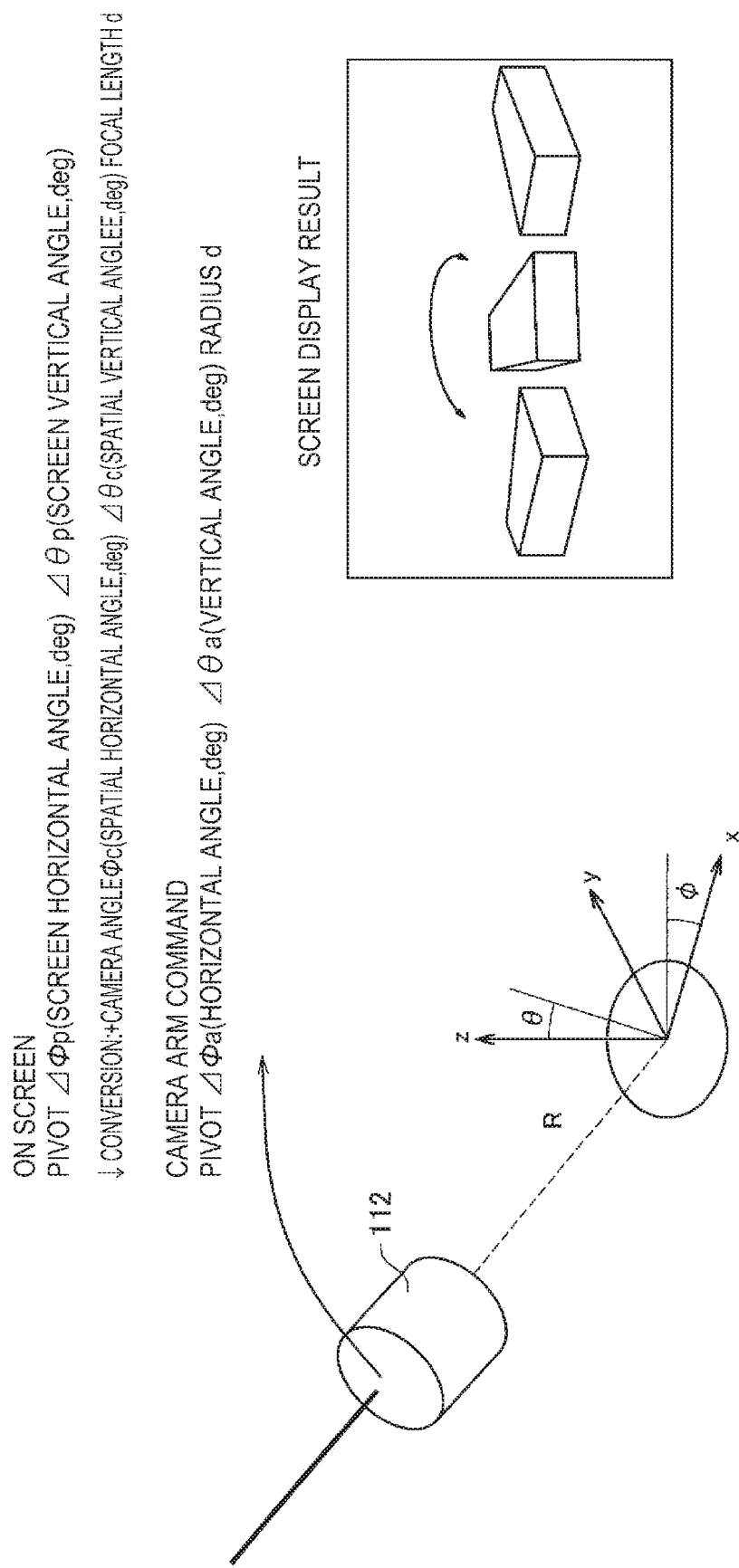
FIG. 8 is a schematic diagram illustrating a conversion method from a command on a screen of a display to a command of a camera arm, in a system of a video microscope.

FIG. 8 illustrates a case in which the pivot command on the screen by the surgeon 20 is converted. The pivot command on the screen is input as a screen horizontal angle $\Delta \Psi p$ and a screen vertical angle $\Delta \theta p$. The pivot command on the screen is converted to the spatial coordinate system by the current camera angle (the screen horizontal angle $\Psi c$, the screen vertical angle $\Delta \Psi c$) and the distance between the camera and the imaging subject (the focal length) d, and is output as the camera arm command. In this case, the camera arm command is $\Delta \Psi a$ (horizontal angle), $\Delta \theta a$ (vertical angle), and radius d.

Figure 9:
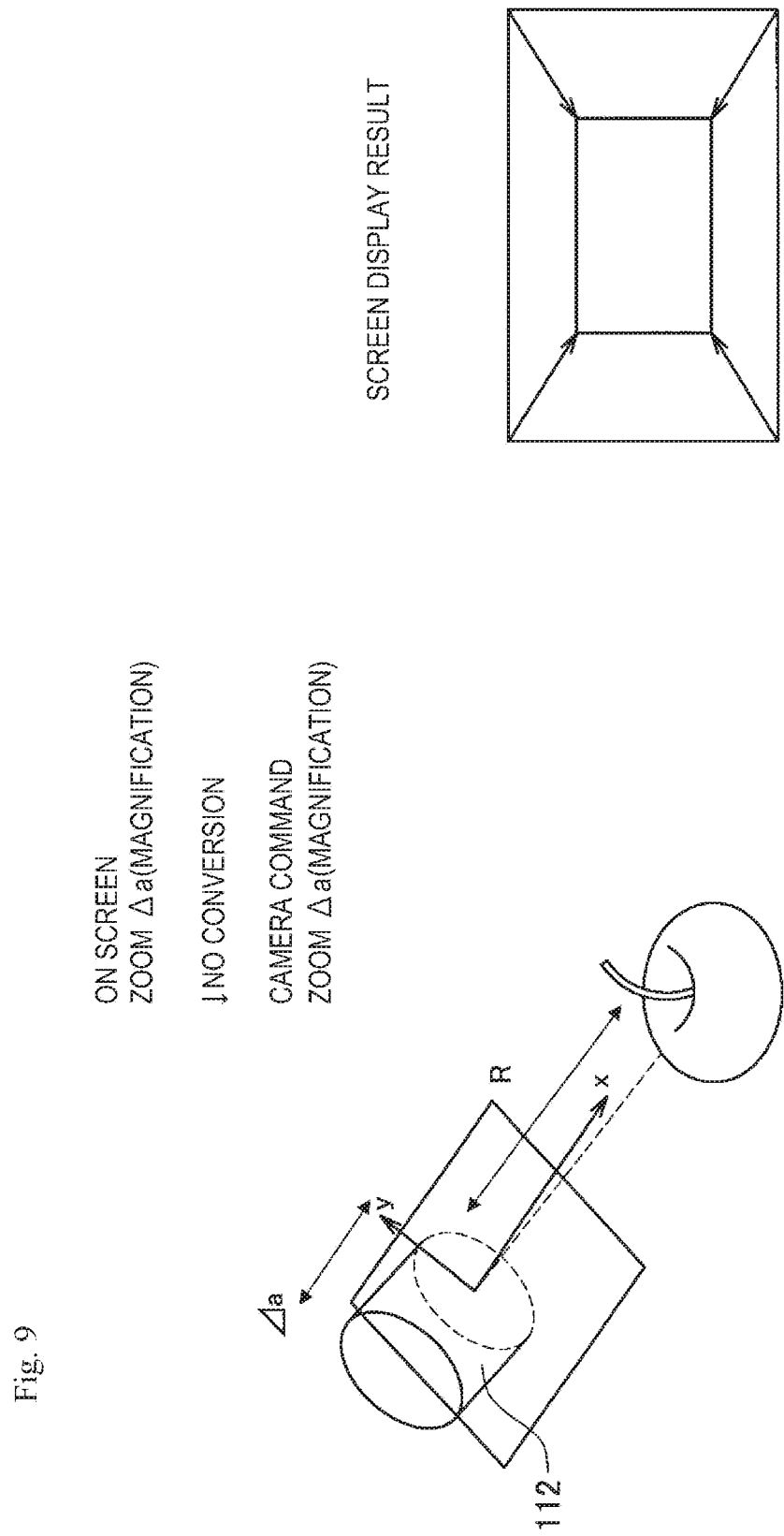
FIG. 9 is a schematic diagram illustrating a conversion method from a command on a screen of a display to a command of a camera arm, in a system of a video microscope.

FIG. 9 illustrates a case of the zoom command on the screen by the surgeon 20. The zoom command on the screen is input as $\Delta a$ (magnification). The zoom command is not converted, but is output as the camera arm command. In this case, the camera arm command is $\Delta a$.

Figure 10:
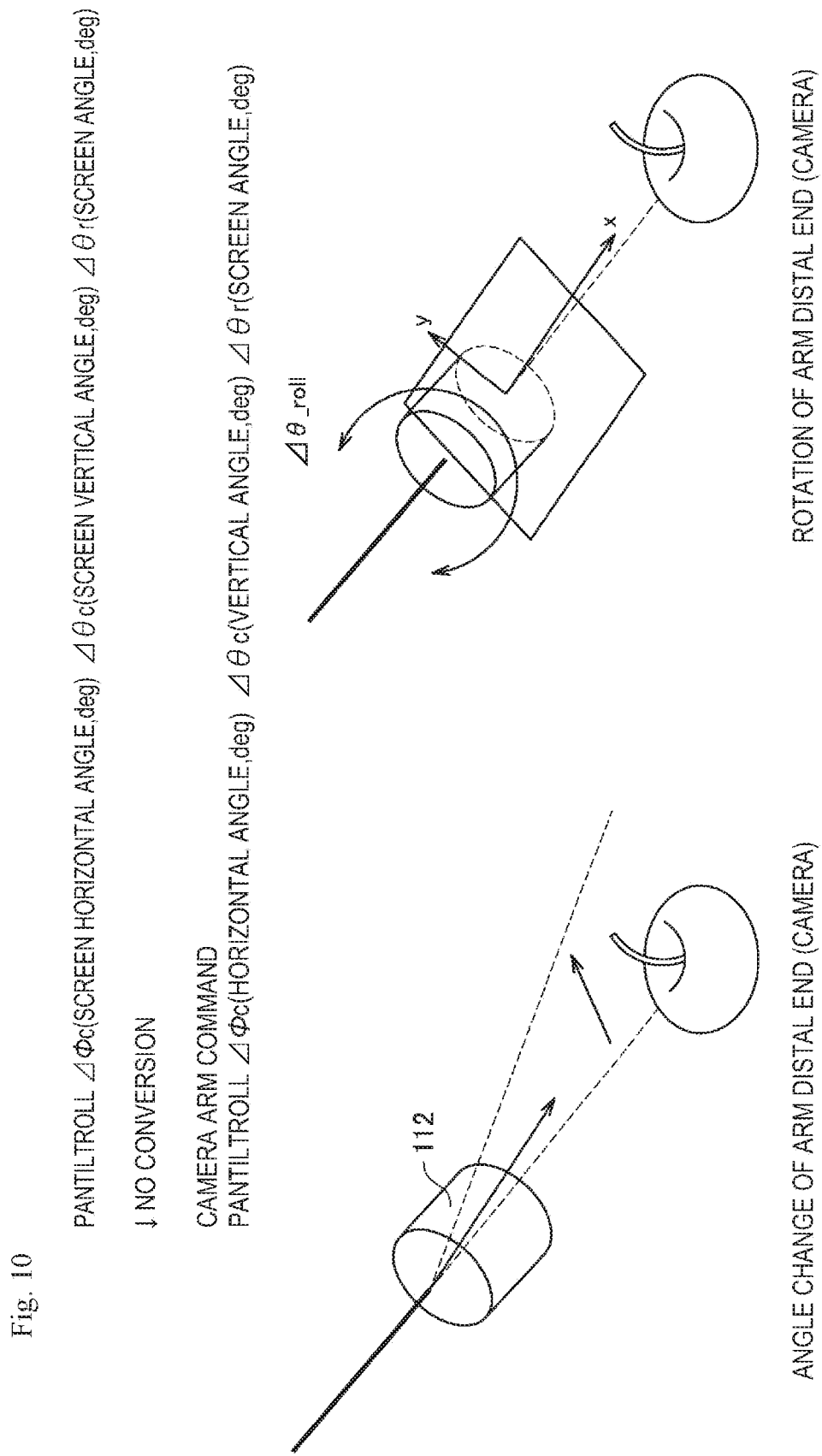
FIG. 10 is a schematic diagram illustrating a conversion method from a command on a screen of a display to a command of a camera arm, in a system of a video microscope.

FIG. 10 illustrates a case of the pan/tilt/roll command. The pan/tilt/roll command is input as $\Delta \Psi c$ (screen horizontal angle), $\Delta \theta c$ (screen vertical angle), and $\Delta \theta r$ (screen angle). In the case of the pan/tilt/roll command as well, the pan/tilt/roll command of the user coordinate system is not converted, but is output as the camera arm command as it is. In this case, the camera arm command is $\Delta \Psi c$ (horizontal angle), $\Delta \theta c$ (vertical angle), and $\Delta \theta r$ (angle).

Figure 11:
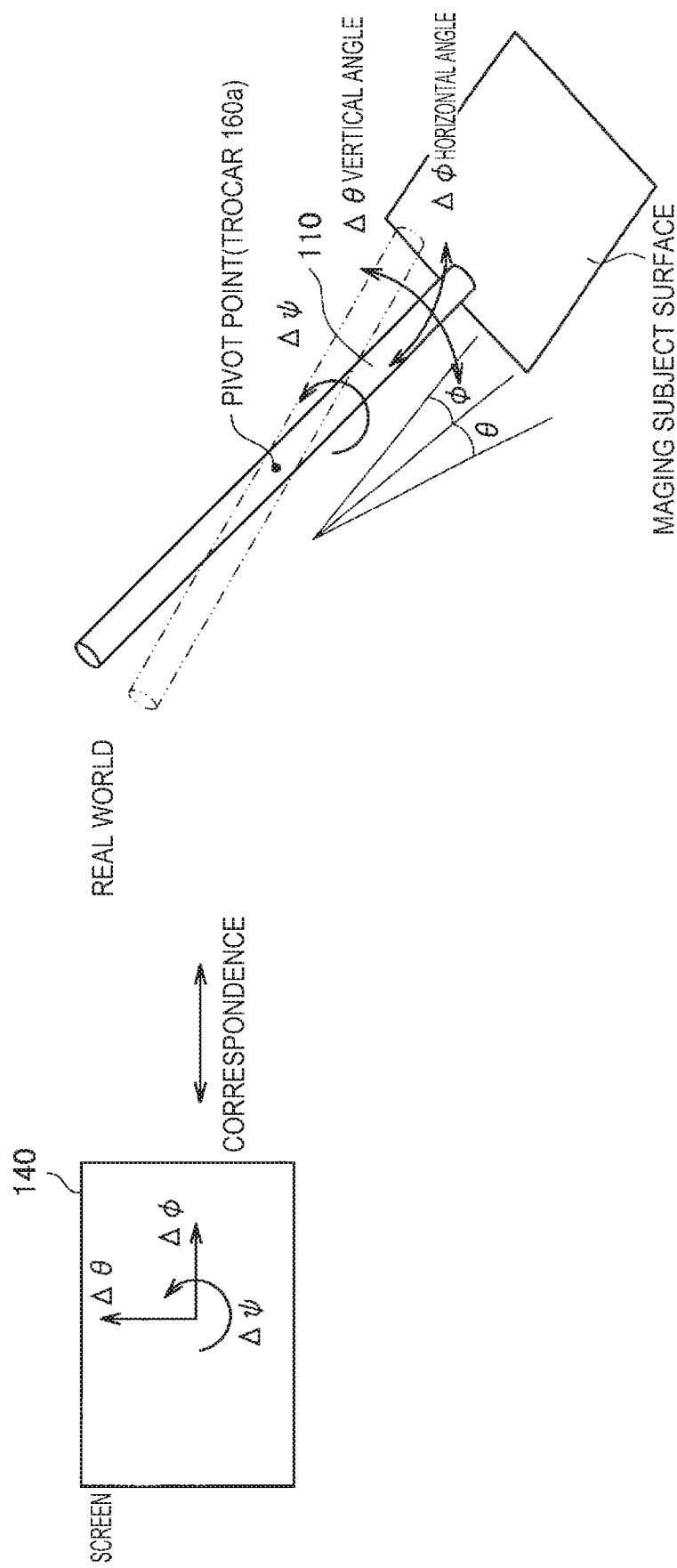
FIG. 11 is a schematic diagram illustrating a conversion method from a command on a screen of a display to a command of a camera arm, in a system of a laparoscope.
Figure 12:
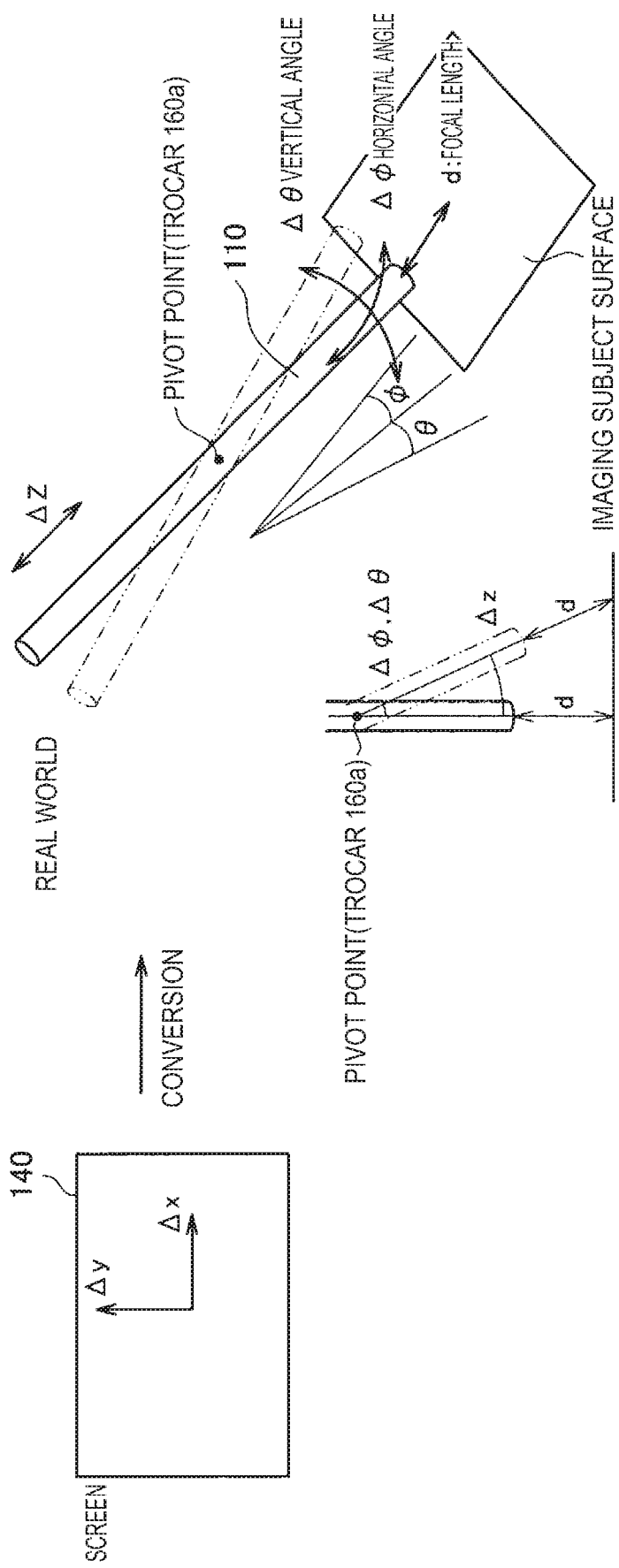
FIG. 12 is a schematic diagram illustrating a conversion method from a command on a screen of a display to a command of a camera arm, in a system of a laparoscope.
Figure 13:
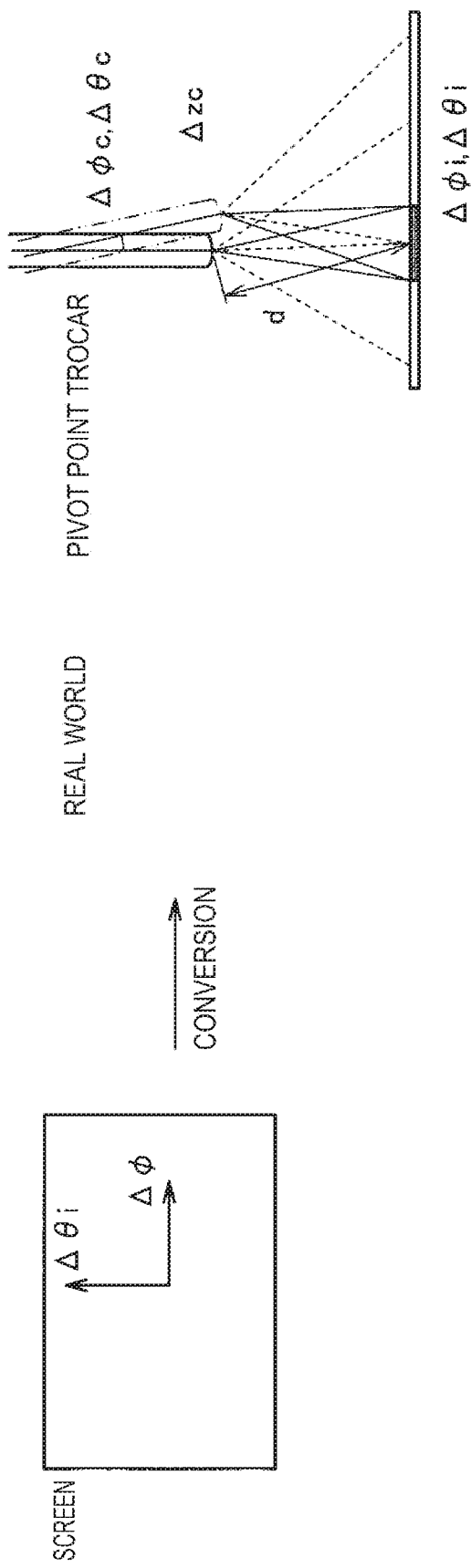
FIG. 13 is a schematic diagram illustrating a conversion method from a command on a screen of a display to a command of a camera arm, in a system of a laparoscope.

FIGS. 11 to 13 are schematic diagrams illustrating a conversion method from the command on the screen of the display 140 to the command of the camera arm, in the system 1000 of the laparoscope 110. FIG. 11 illustrates a case of the pan/tilt/roll command on the screen by the surgeon 20. The pan/tilt/roll command on the screen is input as $\Delta \Psi c$ (screen horizontal angle), $\Delta \theta c$ (screen vertical angle), and $\Delta \theta r$ (screen angle). The pan/tilt/roll command on the screen is converted to the camera arm command by reversing the direction with respect to a pivot point at the trocar 160a, and is output. In this case, the camera arm command is $-\Delta \Psi c$ (horizontal angle), $-\Delta \theta c$ (vertical angle), and $\Delta \theta r$ (angle).

FIG. 12 illustrates a case of the move command on the screen by the surgeon 20. The move command is input as a moving amount ($\Delta X$, $\Delta Y$) on the screen. This change amount ($\Delta X$, $\Delta Y$) is indicated by a proportion (%) in the length in the X direction or the Y direction of the screen. The spatial coordinates of the move command on the screen is converted by the distance d from the distal end of the laparoscope 110 to the imaging subject, and is expressed by a pan/tilt/roll command and a three dimensional move command. In this case, the camera arm command is indicated by the pan/tilt/roll command indicated by $-\Delta \Psi c$ (horizontal angle) and $-\Delta \theta c$ (vertical angle), and the move command indicated by $\Delta z$ (axial direction depth). As described above, assuming that the imaging subject is a flat surface, the translation motion in the depth direction is also performed along with the pan/tilt motion of the move command, in order to maintain the focal length.

FIG. 13 illustrates a case of the pivot command on the screen by the surgeon 20. The pivot command on the screen is input as $\Delta \Psi p$ (screen horizontal angle) and $\Delta \theta p$ (screen vertical angle). The pan/tilt/roll command and the axial direction move command are used as the camera arm command, and a crop command indicating a cut area of electronic zoom is used as the camera command. The pan/tilt/roll command is indicated by $-\Delta \Psi c$ (horizontal angle) and $-\Delta \theta c$ (vertical angle). The move command in the axial direction is indicated by $\Delta z c$ (axial direction depth).

Also, the crop command is indicated by the moving amount (ΔX, ΔY) and the magnification (Δa) on the screen.

In the case of the zoom command on the screen by the surgeon 20, the zoom command on the screen is input as the magnification (Δa). In the case of the laparoscope 110 that does not include the zoom lens, the laparoscope 110 instead adjusts the distance d between the lens tube distal end and the imaging target, in response to the input zoom command on the screen. In this case, the focal length to the visual confirmation target changes, and therefore the move command Δz (axial direction depth) is output as the camera arm command, and the focus command d+ΔR (axial direction focal length) is used as the camera command.

Also, in the case of the electronic zoom command, the moving amount (ΔX, ΔY) and the magnification (Δa) on the screen are input. In this case, the input is not converted, but is output as the camera command.

FIG. 14 is a schematic diagram coordinating a relationship between the commands on the screen illustrated in FIGS. 7 to 13, the camera arm command, and the camera command, with regard to each of zoom, move, pivot, and pan/tilt/roll.

6. Generation of Control Information that Refers to Identification Information

As above, the camera arm 120, the laparoscope 110, and the video microscope 112 behave differently, in response to the command on the screen of the display 140. In the present embodiment, in the video microscope or the video endoscope provided with the camera at the distal end of the camera arm 120, the control of the imaging direction and the frame/zoom of the camera is enabled by the same operation method, regardless of the configuration of the device. When the surgeon 20 instructs a move of the viewpoint by designating the coordinate and the direction on the screen, automatic conversion is performed to fit the actual control condition of the camera and the camera arm, so that the user can operate without being conscious of the configuration of the camera.

Hence, the identification information acquisition unit 590 of the control device 500 acquires the identification information of the camera, when the camera such as the laparoscope 110 and the video endoscope 112 is connected. The acquired identification information is temporarily stored in the memory 592.

The control information generation unit 540 generates the control information with reference to the identification information acquired by the identification information acquisition unit 590, when generating the control information. The identification information includes information indicating the type of the camera, for example information indicating whether the laparoscope 110 or the video microscope 112. Thereby, the command on the screen is converted to the command of the actual behavior, depending on the type of the camera.

An example in which the surgeon 20 inputs a move command of on the screen will be described. In the case of the video microscope 112, the move command on the screen is converted to the spatial coordinate system and is output as the camera arm command (absolute distance; ΔX, ΔY), on the basis of the distance between the camera and the imaging subject (the imaging subject distance d) depending on the state of the camera arm 120 and the zoom factor a depending on the camera state, as illustrated in FIG. 8.

On the other hand, in the case of the laparoscope 110, the zoom command on the screen is converted to the pan/tilt/roll command indicated by −ΔΨc (horizontal angle) and −Δθc (vertical angle) and the camera arm command indicated by the move command indicated by Δz (axial direction depth), as illustrated in FIG. 13. With reference to the identification information stored in the memory 592, the control information generation unit 540 converts the command on the screen to the camera arm command by the method illustrated in FIG. 10 in the case of the video microscope 112, and converts the command on the screen to the camera arm command by the method illustrated in FIG. 13 in the case of the laparoscope 110. Thus, the command on the screen is converted to the command of the actual behavior, depending on the type of the camera.

The move command illustrated in FIG. 8 and the move command illustrated in FIG. 13 are the same as each other in the command designated by the surgeon 20 on the screen, but differ from each other in the camera arm command to the camera arm 120. When the camera arm 120 behaves in accordance with the camera arm command, the motion (move) of the screen on the display 140 are displayed in the same manner in FIG. 8 and FIG. 13. Thereby, the user, such as the surgeon 20, can operate without being conscious of the type of the camera, even when operating either of the laparoscope 110 and the video endoscope 112.

It is desirable that the identification information is transmitted from the camera to the control device 500, when the camera and the control device 500 are connected at the beginning.

Although the above description has illustrated an example in which the control information generated by the control information generation unit 540 differs depending on the difference between the laparoscope 110 and the video endoscope 112, the type of the camera may be subdivided to generate the control information that differs depending on the type of the camera. For example, the laparoscope 110 may be subdivided into a front view scope and an oblique view scope as the type of the camera, to generate the control information on the basis of the identification information of each of the front view scope and the oblique view scope.

Figure 15:
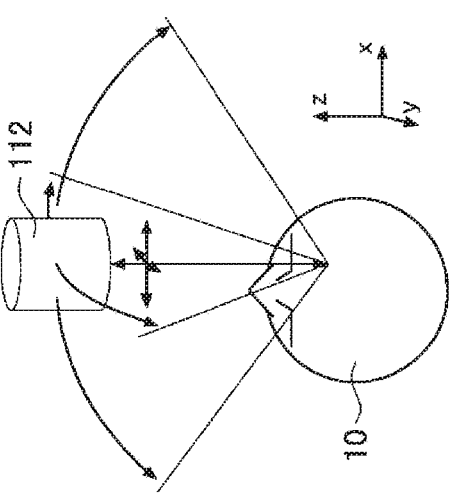
FIG. 15 is a schematic diagram illustrating situations in which a behavior area differs depending on a medical diagnosis and treatment department.

Moreover, different control information can be generated, not only for the type of the camera such as the laparoscope 110 and the video microscope 112, but also for the medical diagnosis and treatment department. FIG. 15 is a schematic diagram illustrating situations in which the behavior area differs depending on the medical diagnosis and treatment department. As illustrated in FIG. 15, in cerebral surgery, the focal length is approximately 30 cm, and the area of the translation (move) is approximately ±4 cm, and the area of the rotation (pivot) is approximately ±45°.

On the other hand, in ophthalmology, the distance z from the lens tube to the target is approximately 20 cm, and the area of the translation (move) is approximately ±3 cm, and the area of the rotation (pivot) is approximately ±60°. Also, in dentistry, the focal length is approximately 30 cm to 40 cm, and the area of the translation (move) is approximately ±8 cm, and the area of the rotation (pivot) is approximately ±45° in the X direction and approximately −70° to 45° in the Y direction.

As described above, the behavior area of the camera differs depending on the medical diagnosis and treatment department. Hence, in the present embodiment, the behavior information corresponding to the medical diagnosis and treatment department is sent to the control device 500 from the camera side, when the camera is connected to the control device 500. The behavior information is stored in the memory 592. Note that the information relevant to the medical diagnosis and treatment department may be input into the control device 500 by the surgeon 20 by using the microphone 170, the keyboard, or the like. When input by using the microphone 170, the information relevant to the medical diagnosis and treatment department is recognized on the basis of voice by the voice recognition unit 522, and is acquired by the identification information acquisition unit 590.

When generating the control information, the control information generation unit 540 generates the control information with reference to the behavior information stored in the memory 592. Thereby, the command on the screen is converted to the command of the actual behavior, depending on the type of the medical diagnosis and treatment department. Thus, the behavior that differs in each medical diagnosis and treatment department is automatically performed. Note that the specifications of neurosurgery and ophthalmology are conceived of, with regard to the application of the video microscope to the medical diagnosis and treatment department. Also, gastroenterological surgery, hepato-biliary-pancreatic surgery, urology, thoracic surgery, gynecology are assumed, with regard to the application of the endoscope to the medical diagnosis and treatment department.

Although the above example has illustrated a rigid endoscope as the laparoscope 110, a flexible scope or an endoscope with a bendable lens tube can also be employed. In this case, an equivalent behavior is performed by handling the move command on the screen, with roll and X or Y direction bending of the flexible lens tube, the roll of the video screen, and conversion from the robot arm command to the move command. An equivalent behavior is performed by handling the pivot command on the screen, with the pan/tilt/roll command and the move command of the camera arm command, roll and X or Y direction bending of the flexible lens tube, and the roll command of the video screen.

As described above, according to the present embodiment, the identification information for identifying the medical device connected to the control device 500 is acquired by the control device 500. Thereby, when the control information is generated by converting the command by the surgeon 20 to the motion of the camera arm and the camera, the control information corresponding to the configuration of various types of medical devices is generated. Thereby, the imaging direction and the frame/zoom of the camera are controlled by the same operation method, regardless of the configuration of the medical device.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to an embodiment of the present disclosure may achieve other effects that are clear to those skilled in the art from the description of this specification.

Additionally, the present technology may also be configured as below.

(1) A control device of a medical system, including:
a recognition unit configured to recognize instruction information for instructing a behavior of an imaging device that is attached to a support arm device to capture an image of a human body;
an identification information acquisition unit configured to acquire identification information related to the imaging device; and
a control information generation unit configured to generate control information for controlling the behavior of the imaging device, on the basis of the instruction information and the identification information.

(2) The control device of a medical system according to (1), in which the control information is generated by converting the instruction information in accordance with the identification information.

(3) The control device of a medical system according to (1) or (2), in which the identification information is information indicating a type of the imaging device.

(4) The control device of a medical system according to (1) or (2), in which the identification information is information indicating a medical diagnosis and treatment department to which the imaging device is applied.

(5) The control device of a medical system according to (4), in which the control information for specifying a behavior area of the support arm device is generated on the basis of the identification information.

(6) The control device of a medical system according to any of (1) to (5), in which the control information includes first control information for controlling the support arm device and second control information for controlling the imaging device.

(7) The control device of a medical system according to any of (1) to (6), in which the imaging device is a video microscope or a video endoscope.

(8) The control device of a medical system according to any of (1) to (7), in which the instruction information is information for instructing any of zoom, move, pivot, and pan/tilt/roll, as the behavior of the imaging device.

(9) The control device of a medical system according to any of (1) to (8), including: a storage unit configured to store the identification information.

(10) A control method of a medical system, including:
recognizing instruction information for instructing a behavior of an imaging device that is attached to a support arm device to capture an image of a human body;
acquiring identification information related to the imaging device; and
generating control information for controlling the behavior of the imaging device, on the basis of the instruction information and the identification information.

(11) A medical system, including:
an imaging device configured to capture an image of a human body;
a support arm device configured to support the imaging device; and
a control device of the medical system including
a recognition unit configured to recognize instruction information for instructing a behavior of the imaging device,
an identification information acquisition unit configured to acquire identification information related to the imaging device, and
a control information generation unit configured to generate control information for controlling the behavior of the imaging device, on the basis of the instruction information and the identification information.

(12) A surgical imaging system, including:
a surgical imaging device including identification information;
a holding arm that holds and controls a position of the imaging device;
a user interface configured to provide non-contact operation of the holding arm; and
processing circuitry configured to control the holding arm according to the identification information and an output of the user interface.

(13) The surgical imaging system according to (12), wherein the imaging device is an endoscope or a microscope.

(14) The surgical imaging system according to (12), wherein the processing circuitry is configured to determine the type of surgical imaging device based on the identification information.

(15) The surgical imaging system according to (12), wherein the processing circuitry is configured to determine at least one of a medical diagnosis or a treatment.

(16) The surgical imaging system according to (12), wherein the processing circuitry is configured to provide imaging control of the surgical imaging device.

(17) The surgical imaging system according to (12), wherein the user interface receives an output from at least one of: a voice recognition device, a sight line detection device, a head tracking device, a gesture recognition device, or a foot switch.

(18) The surgical imaging system according to (17), wherein the voice recognition device includes a microphone to detect a voice input.

(19) The surgical imaging system according to (17), wherein the sight line detection device includes a camera to detect a sight line of the user.

(20) The surgical imaging system according to (19), wherein the camera is provided in eyeglasses worn by the user.

(21) The surgical imaging system according to (17), wherein the head tracking device includes a camera to detect a behavior of the user.

(22) The surgical imaging system according to (17), wherein the gesture recognition device includes a camera to capture gestures of the user.

(23) An image processing apparatus for surgery, including:
processing circuitry configured to control a holding arm that holds and controls a position of an imaging device according to identification information of the imaging device and an output of a user interface configured to provide non-contact operation of the holding arm.

(24) The image processing apparatus for surgery according to (23), wherein the user interface receives an output from at least one of: a voice recognition device, a sight line detection device, a head tracking device, a gesture recognition device, or a foot switch.

(25) The image processing apparatus for surgery according to (23), wherein the imaging device is an endoscope or a microscope.

(26) The image processing apparatus for surgery according to (23), wherein the processing circuitry is configured to determine the type of imaging device based on the identification information.

(27) The image processing apparatus for surgery according to (23), wherein the processing circuitry is configured to determine at least one of a medical diagnosis or a treatment.

(28) The image processing apparatus for surgery according to (23), wherein the processing circuitry is configured to provide imaging control of the imaging device.

(29) A method for controlling an imaging procedure, including:
identifying, using processing circuitry, a surgical imaging device including identification information;
determining a non-contact input of a user; and
controlling a holding arm that holds and controls a position of the surgical imaging device according to the identification information and the determined non-contact input of the user.

(30) The method according to (29), wherein the non-contact input is received from at least one of: a voice recognition device, a sight line detection device, a head tracking device, a gesture recognition device, or a foot switch.

REFERENCE SIGNS LIST 110 laparoscope
112 video endoscope
120 camera arm
500 control device
520 recognition unit
540 control information generation unit
590 control information acquisition unit
592 memory

The invention claimed is:

1. A surgical imaging system, comprising:
a surgical imaging device including identification information;
a holding arm that holds and controls a position of the surgical imaging device;
a user interface configured to provide non-contact operation of the holding arm; and
processing circuitry configured to
determine a behavior area that corresponds with a particular medical diagnosis or a treatment,
identify movement parameters of the holding arm that define at least an amount of rotation and translation of the holding arm used in the particular medical diagnosis or treatment according to the surgical imaging device identified by the identification information,
automatically control a movement of the holding arm within a movement range defined by the movement parameters for the particular medical diagnosis or the treatment and according to the identification information and an output of the user interface that provides non-contact control of the holding arm,
wherein different movement parameters are pre-established for different surgical imaging devices and different medical diagnoses or treatments.

2. The surgical imaging system of claim 1, wherein the imaging device is an endoscope or a microscope.

3. The surgical imaging system of claim 1, wherein the processing circuitry is configured to determine the type of surgical imaging device based on the identification information.

4. The surgical imaging system of claim 1, wherein the processing circuitry is configured to determine the particular medical diagnosis or treatment.

5. The surgical imaging system of claim 1, wherein the processing circuitry is configured to provide imaging control of the surgical imaging device.

6. The surgical imaging system of claim 1, wherein the user interface receives an output from at least one of:
a voice recognition device,
a sight line detection device,
a head tracking device,
a gesture recognition device, or
a foot switch.

7. The surgical imaging system of claim 6, wherein the voice recognition device includes a microphone to detect a voice input.

8. The surgical imaging system of claim 6, wherein the sight line detection device includes a camera to detect a sight line of the user.

9. The surgical imaging system of claim 8, wherein the camera is provided in eyeglasses worn by the user.

10. The surgical imaging system of claim 6, wherein the head tracking device includes a camera to detect a behavior of the user.

11. The surgical imaging system of claim 6, wherein the gesture recognition device includes a camera to capture gestures of the user.

12. An image processing apparatus for surgery, comprising:
processing circuitry configured to
determine a behavior area that corresponds with a particular medical diagnosis or a treatment,
identify movement parameters of the holding arm that define at least an amount of rotation and translation of the holding arm used in the particular medical diagnosis or treatment according to the surgical imaging device identified by the identification information,
automatically control a movement of a holding arm that holds and controls a position of an imaging device within a movement range defined by the movement parameters for the particular medical diagnosis or the treatment and according to identification information of the imaging device and an output of a user interface that provides non-contact control of the holding arm, wherein different movement parameters are pre-established for different surgical imaging devices and different medical diagnoses or treatments.

13. The image processing apparatus of claim 12, wherein the user interface receives an output from at least one of:
a voice recognition device,
a sight line detection device,
a head tracking device,
a gesture recognition device, or
a foot switch.

14. The imaging processing apparatus of claim 12, wherein the imaging device is an endoscope or a microscope.

15. The imaging processing apparatus of claim 12, wherein the processing circuitry is configured to determine the type of imaging device based on the identification information.

16. The imaging processing apparatus of claim 12, wherein the processing circuitry is configured to determine the particular medical diagnosis or treatment.

17. The imaging processing apparatus of claim 12, wherein the processing circuitry is configured to provide imaging control of the imaging device.

18. A method for controlling an imaging procedure, comprising:
identifying, using processing circuitry, a surgical imaging device including identification information;
determining, using the processing circuitry, a behavior area that corresponds with a particular medical diagnosis or a treatment;
identifying, using the processing circuitry, movement parameters of a holding arm that define at least an amount of rotation and translation of the holding arm used in the particular medical diagnosis or treatment according to the surgical imaging device identified by the identification information;
determining a non-contact input of a user; and
automatically controlling the holding arm that holds and controls a position of the surgical imaging device within a movement range defined by the movement parameters for the particular medical diagnosis or the treatment and according to the identification information and the determined non-contact input of the user, wherein different movement parameters are pre-established for different surgical imaging devices and different medical diagnoses or treatments.

19. The method of claim 18, wherein the non-contact input is received from at least one of:
a voice recognition device,
a sight line detection device,
a head tracking device,
a gesture recognition device, or
a foot switch.

* * * * *